(12) United States Patent
Marcelis et al.

(10) Patent No.: US 11,554,273 B2
(45) Date of Patent: Jan. 17, 2023

(54) PHANTOM AND METHOD FOR THE QUALITY ASSURANCE OF A HADRON THERAPY APPARATUS

(71) Applicant: Ion Beam Applications, S.A., Louvain-la-Neuve (BE)

(72) Inventors: Simon Marcelis, Louvain-la-Neuve (BE); Séverine Rossomme, Louvain-la-Neuve (BE); Gaylor Deroissart, Louvain-la-Neuve (NL); Jochen Krimmer, Louvain-la-Neuve (DE)

(73) Assignee: Ion Beam Applications, S.A., Louvain-la-Neuve (BE)

( * ) Notice: Subject to any disclaimer, the term of this patent is extended or adjusted under 35 U.S.C. 154(b) by 376 days.

(21) Appl. No.: 16/900,133

(22) Filed: Jun. 12, 2020

(65) Prior Publication Data
US 2020/0391055 A1    Dec. 17, 2020

(30) Foreign Application Priority Data

Jun. 13, 2019 (EP) ..................................... 19180094
Jul. 9, 2019 (EP) ..................................... 19185261

(51) Int. Cl.
*A61N 5/10*    (2006.01)
(52) U.S. Cl.
CPC .... *A61N 5/1075* (2013.01); *A61N 2005/1076* (2013.01); *A61N 2005/1087* (2013.01)
(58) Field of Classification Search
CPC .... A61N 2005/1076; A61N 2005/1085–1098; A61N 5/1075; A61N 5/10–1084
See application file for complete search history.

(56) References Cited

U.S. PATENT DOCUMENTS 9,901,751 B1 * 2/2018 Boisseau .............. H05K 9/0049
2008/0217561 A1    9/2008 Mackie et al.
(Continued)

FOREIGN PATENT DOCUMENTS

EP           1967229 A1    9/2008
WO    WO-2013/160379 A1    10/2013
WO    WO-2016/170115 A1    10/2016

OTHER PUBLICATIONS

International Search Report received in European Patent Application No. EP 19185261 (four pages).

*Primary Examiner* — Thaddeus B Cox
(74) *Attorney, Agent, or Firm* — Finnegan, Henderson, Farabow, Garrett & Dunner, LLP (57) ABSTRACT

The disclosure provides a phantom and method for quality assurance of a hadron therapy apparatus used in the intensity modulated particle therapy mode. The phantom comprises a frame structure comprising a base plate, one or more energy wedges, an energy wedge first face inclined with respect to said base plate and an energy wedge second face perpendicular to said base plate, said one or more energy wedges being mounted on said base plate, a 2D detector; said one or more wedges, and 2D detector being in known fixed positions in relation to said frame structure. Said phantom comprises in addition a Spread-Out Bragg Peak wedge, said SOBP wedge having an SOBP wedge first face inclined with respect to said base plate, and a SOBP wedge second face, perpendicular to said base plate, said SOBP wedge being made of a material having a relative density higher than 1.3 preferably 1.5, more preferably 1.7, the distance between the SOBP wedge first face and SOBP second face varying between the penetration depth of a beam having an energy between the high and low limit energy of the beam of said hadron therapy apparatus. The disclosure also provides a (Continued)

method for determining the compliance of the planned SOBP with the actual SOBP.

16 Claims, 7 Drawing Sheets

(56) References Cited

U.S. PATENT DOCUMENTS

| | | |
|---|---|---|
| 2015/0168563 A1 | 6/2015 | Lee et al. |
| 2016/0155365 A1* | 6/2016 | Tanabe .................. G09B 23/32 434/272 |
| 2017/0322316 A9 | 11/2017 | Nelson |
| 2018/0098745 A1* | 4/2018 | Marcelis ................ A61B 6/584 |

* cited by examiner

PHANTOM AND METHOD FOR THE QUALITY ASSURANCE OF A HADRON THERAPY APPARATUS

CROSS-REFERENCE TO RELATED APPLICATIONS

This application claims the benefit of European Patent Application No. 19180094.5, filed Jun. 13, 2019, and European Patent Application No. 19185261.5, filed Jul. 9, 2019, the contents of each of which are hereby incorporated by reference in their entirety.

The present disclosure is related to the field of hadron therapy. More particularly, the disclosure is related to a phantom and method for quality assurance of a hadron therapy apparatus used in the intensity modulated particle therapy (IMPT) mode also known as pencil beam scanning (PBS) technique.

BACKGROUND

Hadron therapy comprises the treatment of a tumour by irradiation with an energetic hadron beam. Preferred hadrons are typically protons and carbon ions. In current proton beam facilities, the Pencil Beam Scanning technique (PBS) involves the irradiation of separate spots in a target, each spot having a predefined position and depth, with a predefined dose being prescribed for each spot. In each treatment room of the facility, various characteristics of the delivered beam are subjected to a daily verification routine. These characteristics may comprise:

- beam range: the position (depth) of the Bragg peak at a given beam energy in a given target, usually a water phantom or multi-layer ionization chamber;
- spot position, spot size and spot symmetry, measured by a suitable 2D-detector, for example an array of ionization chambers or a scintillator screen equipped with a CCD camera;
- the deposited dose, measured by an absolute ionization chamber, for checking the output factor of the irradiation installation;
- the position of the proton beam with respect to the X-ray imaging system;
- when a Spread-out Bragg peak (SOBP) is used, the compliance of the planned SOBP to the actual SOBP.

Each of these characteristics are commonly measured at a number of distinct beam energy levels, by a separate measurement device. A complete verification may involve many manual operations, including entrance in the treatment room for adapting a phantom or a measuring device. Therefore, the time needed to complete a verification routine is in the order of 30 to 60 minutes. Such long verification times are reducing the efficiency of the treatment facility in terms of the number of treatments that may be performed per day. Typical times spent on quality assurance (QA) in a proton beam facility are as follows: daily QA: 30 minutes, i.e 16 days per year in total; monthly QA: 3 hours per month, i.e. 4.5 days per year in total; yearly QA 16 hours, i.e. 2 days per year. It is therefore important to reduce the time needed for performing daily QA.

A Phantom and Method for Quality Assurance of a Particle Therapy Apparatus is known from PCT Pat. publication No. WO 2016/170115. This phantom may comprise a frame structure; one or more wedges, a first and second block of material each having a first block face and a second block face parallel thereto, an absolute dosimeter arranged at said first block face, a plurality of beads of high density material located in said blocks and a 2D detector. The components may be arranged in a known fixed position in relation to the frame structure. A central bead is maintained in a central known fixed position in relation to the frame structure. The components may be arranged in the frame structure so that a beam will traverse the phantom, through the central bead, without traversing any material besides said central bead. The product "Sphinx PT" provided by IBA Dosimetry is built according to this document. The wedges of this phantom are made of a water-equivalent materiel, i.e. RW3, having a relative density of 1,045. This phantom is preferably used with a 2D detector having a scintillator screen and a CCD camera.

SUMMARY

Embodiments of the present disclosure may provide a phantom and method for quality assurance of a hadron therapy apparatus used in the intensity modulated particle therapy (IMPT) mode, allowing to perform a fast and reliable verification of the particle therapy apparatus. More precisely, there is a need for a phantom allowing performing the verification of the compliance of the planned SOBP with the actual SOBP, while minimizing the time and effort needed to perform the verification.

In some embodiments, there is provided a phantom for quality assurance of a hadron therapy apparatus usable in the intensity modulated particle therapy (IMPT) mode, said hadron therapy apparatus being configured for producing a hadron beam having an energy comprised between a low energy limit and a high energy limit. The phantom may comprise:

a) a frame structure comprising a base plate, the base plate having a first edge and a second edge parallel to said first edge;
b) one or more energy wedges each having an energy wedge base face, an energy wedge first face inclined with respect to said energy wedge base face and an energy wedge second face perpendicular to said energy wedge base face, said one or more energy wedges being mounted on said base plate, said energy wedge second face being parallel to said second edge;
c) a 2D detector arranged at said second edge, and being mounted perpendicular to said base plate;

said one or more wedges, and 2D detector being in known fixed positions in relation to said frame structure. According to the disclosure, the phantom may comprise a Spread-Out Bragg Peak (SOBP) wedge, said SOBP wedge having a SOBP wedge base face, an SOBP wedge first face inclined with respect to said SOBP wedge base face, and a SOBP wedge second face, perpendicular to said SOBP wedge base face, said SOBP wedge being mounted on said base plate, said SOBP wedge second face being parallel to said second edge, said SOBP wedge being made of a material having a relative density higher than 1.3, preferably higher than 1.5, more preferably higher than 1.7, a said first and said second SOBP wedge face, measured along a line parallel to said SOBP wedge base face varying between zero and the penetration depth in said material of a hadron beam having an energy equal to said high energy limit.

Hadron therapy apparatuses, when using proton beams, typically produce beams having an energy in the range of 35 MeV to 230 MeV. When carbon ions are used, the energy of the beam typically is in the range of 100 Mev/nucleon to 400 MeV/nucleon.

At least one of said energy wedges may be made of same material having a relative density higher than 1.3, preferably higher than 1.5, more preferably higher than 1.7.

Said material may be selected from polyvinylidene fluoride, polyimides, polyetheretherketone polymers and mixtures thereof, known respectively as PVDF, PI, PEEK.

The frame structure may advantageously comprise one or two handles affixed to the base plate and to the 2D detector.

The 2D detector may comprise an amorphous silicon active flat panel detector.

The base plate and one or more of said wedge base faces and/or said SOBP wedge base face may comprise securing means for fixing said wedges to said base plate.

A distance between said first and said second energy wedge face of one of said energy wedges, measured along a line parallel to said energy wedge base face may be the penetration depth in said material of a hadron beam having a nominal energy between said high energy limit, and said low energy limit, at mid height of said wedge, and may be less than 15 mm at the bottom height of said wedge, and less than 15 mm higher at the top height of said energy wedge, the height being measured perpendicularly to said energy wedge base face.

In some embodiments, there is provided a method for quality assurance of a hadron therapy apparatus, usable in the intensity modulated particle therapy (IMPT) mode, wherein said apparatus may comprise a patient positioner having a reference position, using a phantom according to the disclosure, the method comprising:
  a) positioning the phantom on said patient positioner;
  b) irradiating the phantom with a modulated beam, said modulated beam comprising a plurality of beams each having a different energy and having a dose selected in order to produce an SOBP in matter, said modulated beam being directed at said SOBP wedge first face, in a direction parallel to the SOBP wedge base face and at a height measured perpendicularly to said SOBP wedge base face;
  c) acquiring an image of said modulated beams on said 2D detector;
  d) repeating the step of irradiating and the step of acquiring for a plurality of heights between the bottom height of said SOBP wedge, and the top height of said SOBP wedge;
  e) from said plurality of responses at each height, reconstructing the SOBP.

Thereby, the compliance of the planned SOBP with the actual SOBP may be determined.

In some embodiments, there is provided a computer program comprising code for performing steps c) to f) of the method of the disclosure.

In some embodiments, there is provided a system comprising a phantom according to the disclosure and a controller comprising a computer program according to the disclosure, for the quality assurance of a hadron therapy apparatus.

SHORT DESCRIPTION OF THE DRAWINGS

These and further aspects of the present disclosure will be explained in greater detail by way of example and with reference to the accompanying drawings in which.

The drawings of the figures are neither drawn to scale nor proportioned. Generally, identical components are denoted by the same reference numerals in the figures.

DETAILED DESCRIPTION

Figure 1:
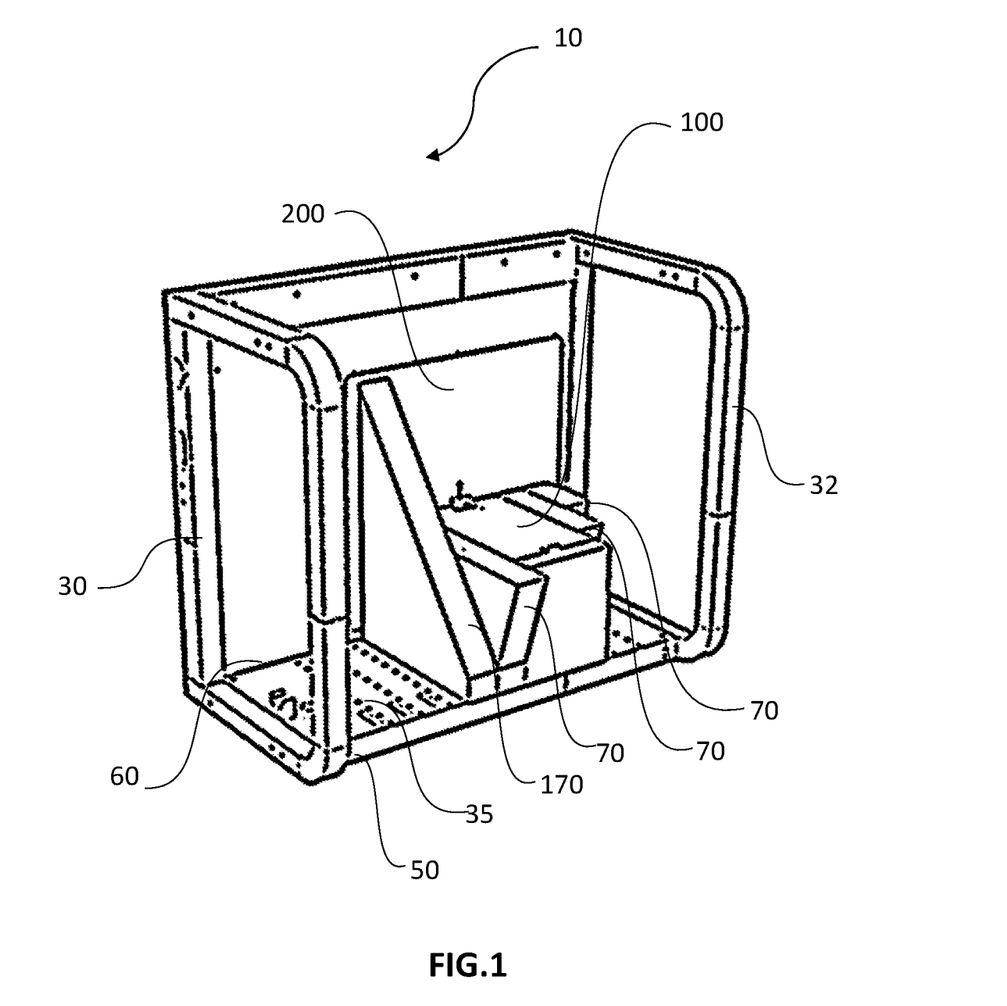
FIG. 1 is a perspective view of a phantom according to an embodiment of the disclosure.

FIG. 1 is a perspective view of a phantom 10 according to one embodiment of the present disclosure. A frame structure 30 may include a base plate 35, having a first edge 50, and a second edge 60. A plurality of elements may be mounted on the base plate: Energy wedges 70, an SOBP wedge 170, a block of material 100. Three energy wedges are represented but more or less energy wedges may be used. An SOBP wedge 170 is also present. A block of material 100 may be used for supporting an absolute dosimeter and/or markers for positioning the phantom. A 2D detector may be arranged at the second edge 60 of the base plate 35 and mounted perpendicularly thereto. One or two handles 32 may be arranged at the lateral sides of the phantom 10, in order to facilitate the handling, and to improve the stiffness of the phantom 10.

The SOBP wedge 170, and optionally of the energy wedges 70 may be made of a material having a relative density higher than 1.3, preferably higher than 1.5, preferably higher than 1.7. The applicant has determined that a suitable material for these wedges may be polyvinylidene fluoride also known as PVDF. Use of a water-equivalent material such as RW3, known from prior art phantoms would require a large size for the SOBP wedge, leading to difficulties in handling the phantom. A relative density at or above 1.7 was found suitable for obtaining a phantom having a preferred size. Metals where found unsuitable because of the activation produced by the hadron beam. PTFE (Teflon) was found unsuitable because it is not radiation-resistant. Graphite was also found unsuitable because it became brittle under irradiation. Polyvinylidene fluoride was found to meet all requirements regarding density, radiation hardness and mechanical properties. Other suitable materials are polyimide polymers. Polyimide polymers have densities in the range of 1.3 to 1.4. A suitable polyimide polymer is sold under the brand name TECASINT by Ensinger Plastics. Other suitable materials are PEEK (Polyetheretherketone) materials. The PEEK material sold by Ensinger Plastics under the brand name TECAPEEK has a relative density of 1.31 and was also found suitable.

The 2D-detector may advantageously be a flat panel usable for X-ray imaging. Such panels may have a matrix of 1024×1024 sensor cells, each comprising a diode as sensor and a TFT (Thin film transistor) for addressing the lines and transmit the signals. At a pitch of 200 µm, such a panel has a sensitive area of 200 mm×200 mm. When using protons or carbon ions, the scintillator used for X-ray imaging may be removed. A suitable flat panel is the XRD 0822 AO, AP provided by Perkin Elmer.

Figure 2A:
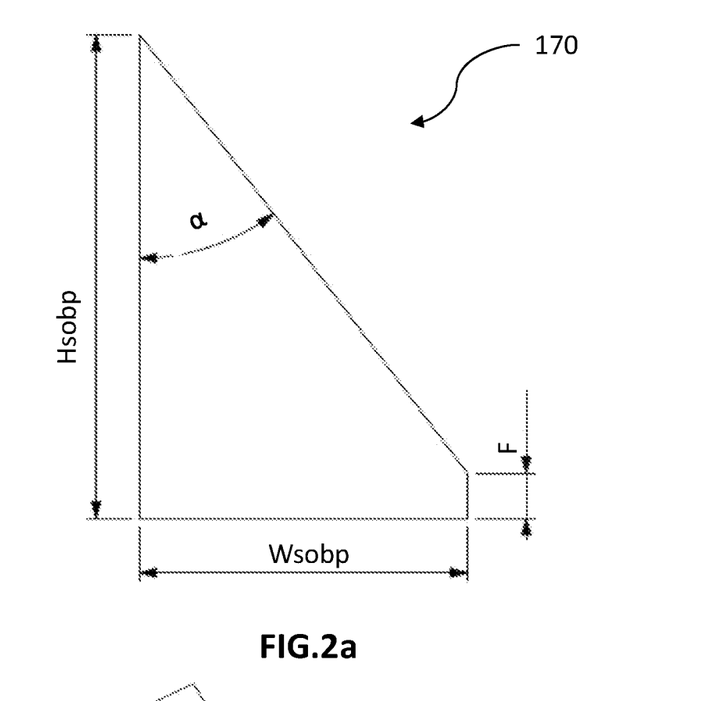
FIGS. 2a and 2b are a side view and a perspective view of an SOBP wedge.
Figure 2B:
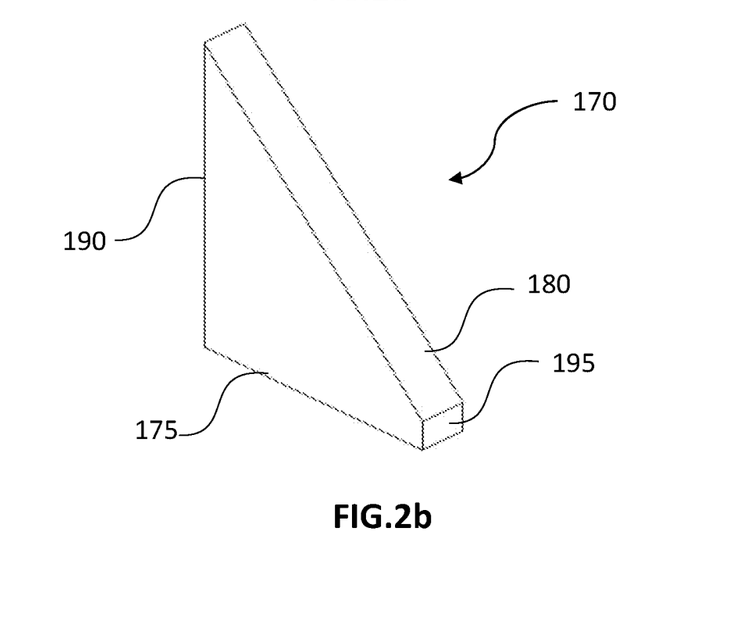

FIGS. 2a and 2b are a side and perspective view of an SOBP wedge 170. The width Wsobp of the SOBP wedge 170 at its basis is determined in order that a pencil beam directed along this width, from the first face 180 to the second face 190 and parallel to the base 175 of the SOBP wedge 170, will have a Bragg peak inside the SOBP wedge, upstream of the second face 190 of the SOBP wedge 170. The height Hsobp of the SOBP wedge is determined in order that a beam directed at the top of the SOBP wedge will reach the upper region of the 2D detector 200. When a material having a relative density of 1.7 is selected, such as PVDF, a value of
Wsobp=151 mm
for use with a hadron therapy apparatus using protons up to an energy of 230 MeV was found suitable. The skilled person will know how to determine the value of Wsobp for other ions, other energies and other relative densities of the material. The SOBP wedge base 195 is used for fixing the wedge to the base plate, as described hereunder. A typical 2D detector may have a sensitive area of 200 mm×200 mm. Therefore, the height Hsobp, may be 220 mm, including a height F of 20 mm for the SOBP wedge base 195. The thickness of the SOBP wedge 170 may be in the range of 20 mm to 30 mm. The value selected was 28 mm. The angle α, for the SOBP wedge depicted is 36.7°.

Figure 3A:
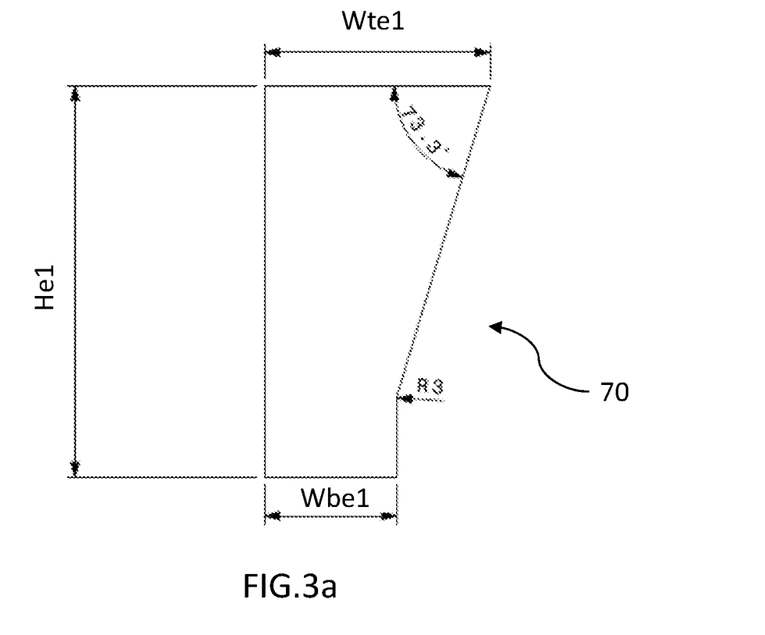
FIGS. 3a and 3b are a side view and a perspective view of an energy wedge for a first nominal energy.
Figure 3B:
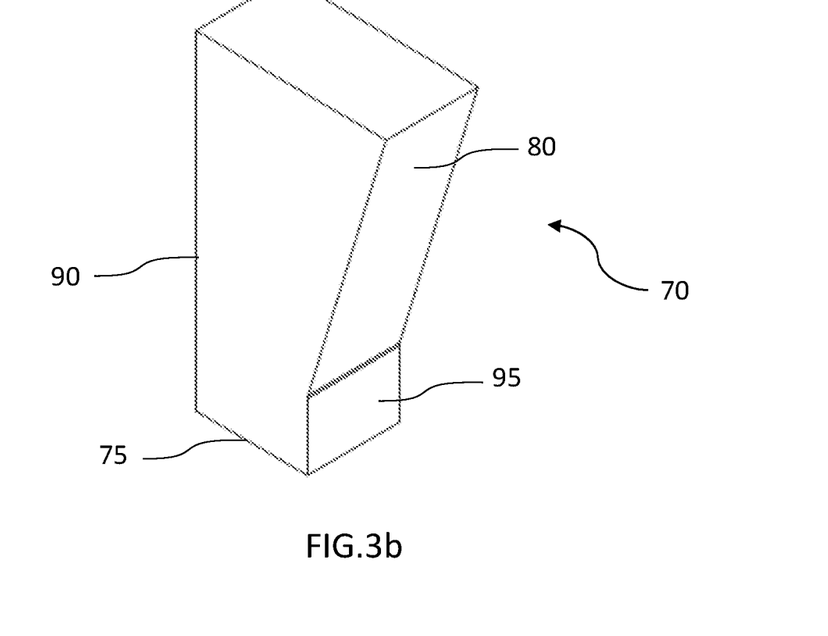

FIGS. 3a and 3b, 4a and 4b, 5a and 5b are a side views and perspective views of energy wedges for a three nominal energies. The purpose of these energy wedges may be the precise determination of the energy of a pencil beam having a nominal energy. Referring to FIGS. 3a and 3b, the energy wedge 70 may have an energy wedge first face 80 (beam entry), and energy wedge second face 90 (beam exit), and an energy wedge base face 75. The energy wedge base 95 may be used for fixing the wedge to the base plate, as described hereunder.

Figure 4A:
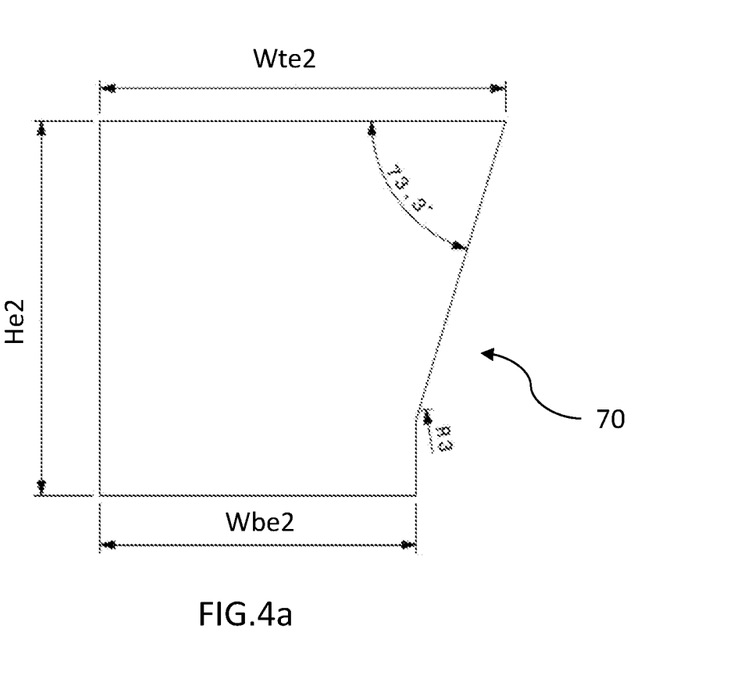
FIGS. 4a and 4b are a side view and a perspective view of an energy wedge for a second nominal energy.
Figure 4B:
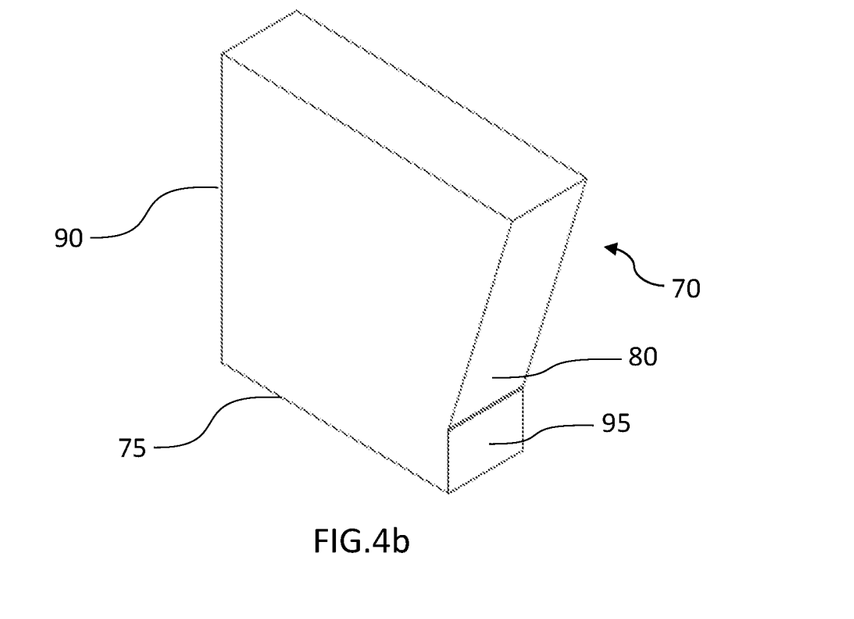
Figure 5A:
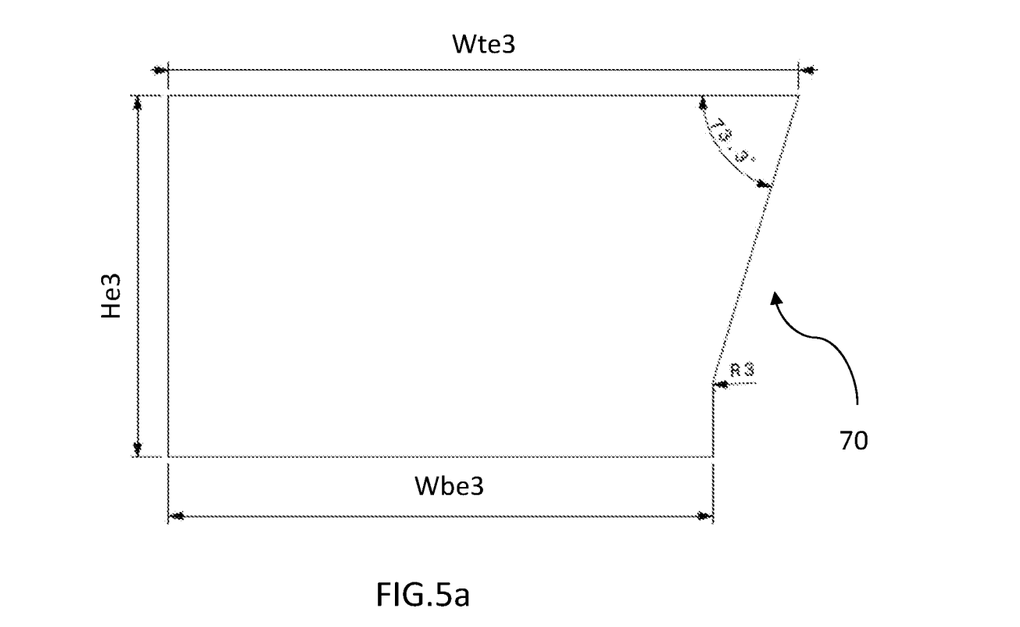
FIGS. 5a and 5b are a side view and a perspective view of an energy wedge for a third nominal energy.
Figure 5B:
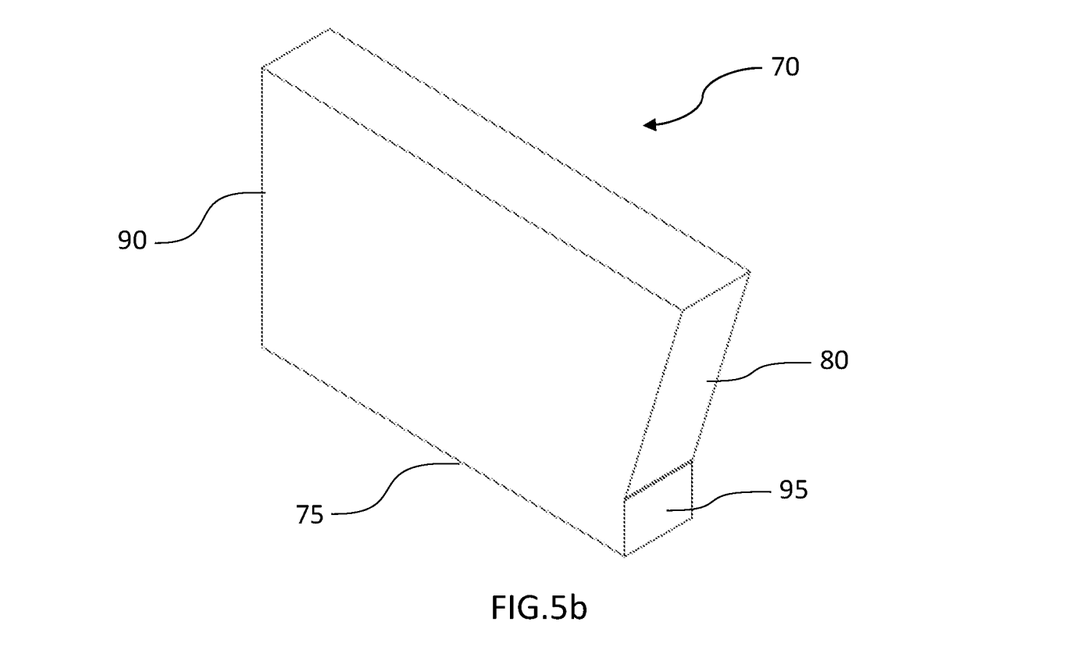

The energy wedges of FIG. 4 and FIG. 5 are similar, but with different sizes. The heights He1, He2, He3 of the three energy wedges are equal to 100 mm, including the height of the energy wedge base 95 of 20 mm. The widths of the base Wbei and of the top Wtei, of the energy wedges may be as follows:

| WEDGE | NOMINAL ENERGY MeV | Wbei mm | Wtei mm |
| --- | --- | --- | --- |
| 1 | 100 | 34 | 58 |
| 2 | 150 | 85 | 109 |
| 3 | 200 | 151 | 175 |

The thickness of the energy wedge 70 may also be in the range of 20 mm to 30 mm. The value selected was 28 mm, being the same as the SOBP wedge.

Preferably, the SOBP wedge, the energy wedges, and other components of the phantom, such as the block of material 100 may be fastened to the base plate 35 of the frame structure 30. In one embodiment of these securing means, the components, have a base section 195 (for the SOBP wedge) or 95 (for the energy wedges). Holes are drilled in the base plate 35 and corresponding holes are drilled in the base sections. The components may then be fastened with screws. The lengths of the screws are limited to the bottom region of the components so that the beams are not disturbed by these screws. A height of 20 mm was found suitable, represented by F on FIG. 2a. Holes and screws having a diameter of 4 mm were used and found convenient. Other fastening may be conceived. Successive rows of holes may be drilled in the base plate, at a distance corresponding to the thickness of the wedges, i.e. 28 mm, in order to give modularity, and allow various combinations of wedges.

Figure 6:
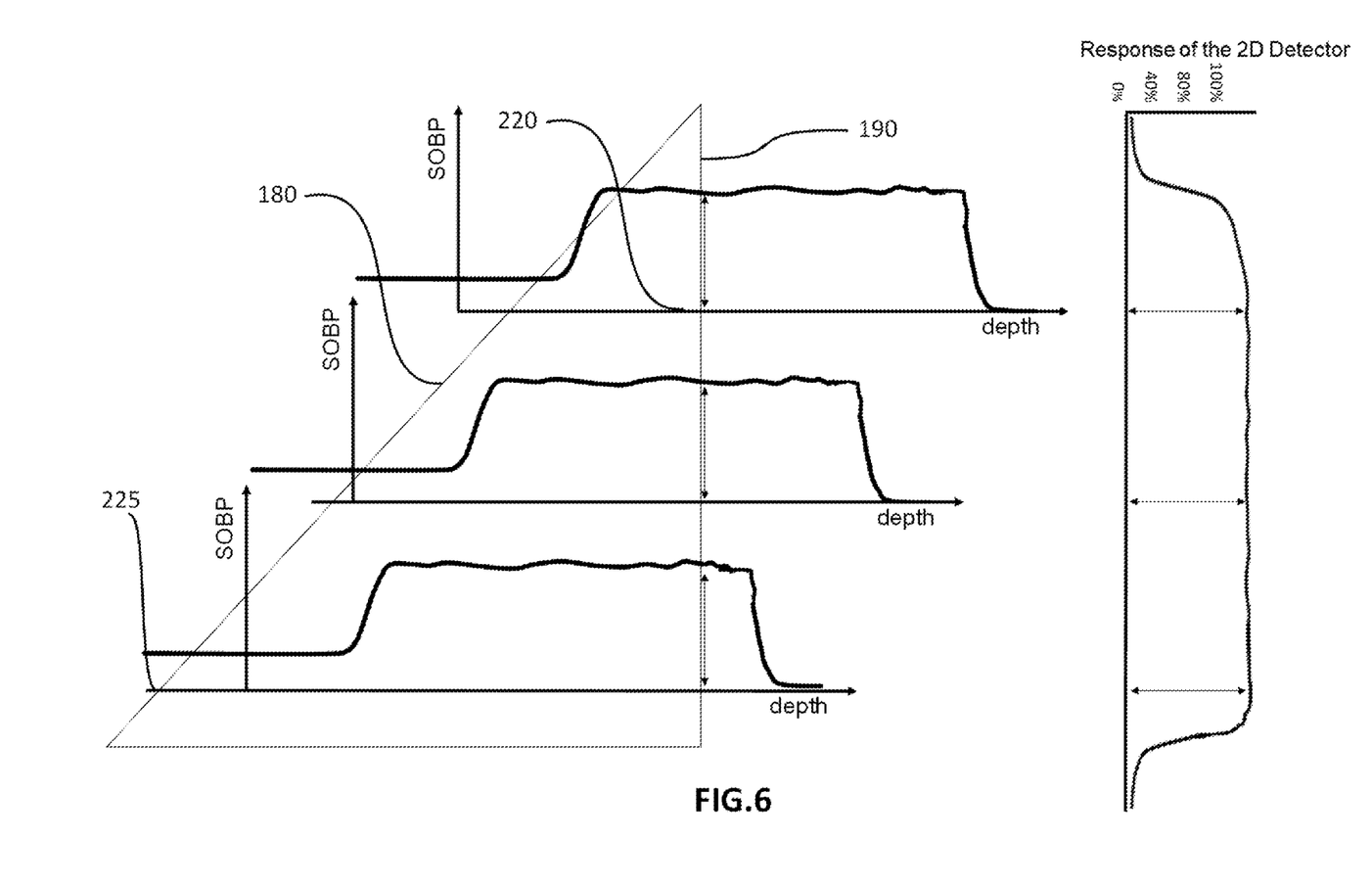
FIG. 6 is a schematic view of a modulated beam configured for producing an SOBP, traversing the SOBP wedge, at different heights.

FIG. 6 is a schematic view of a modulated beam configured for producing an SOBP, traversing the SOBP wedge, at different heights. A modulated beam 220 is depicted at three different heights, entering the SOBP wedge first face 180 at three entry point 225, 225', 225" and exiting the SOBP wedge at the SOBP wedge second face 190, where they impinge the 2D detector. Therefore, the response of the 2D detector for that modulated beam, at that height, corresponds to the value of the SOBP for a depth corresponding to the width of the SOBP wedge at that height in the material of the SOBP wedge. For each modulated beam, the value representative of the response of the 2D detector, in function of the penetration depth in the wedge, is represented at the right-hand side of FIG. 6, and represents the shape of the SOBP.

Figure 7:
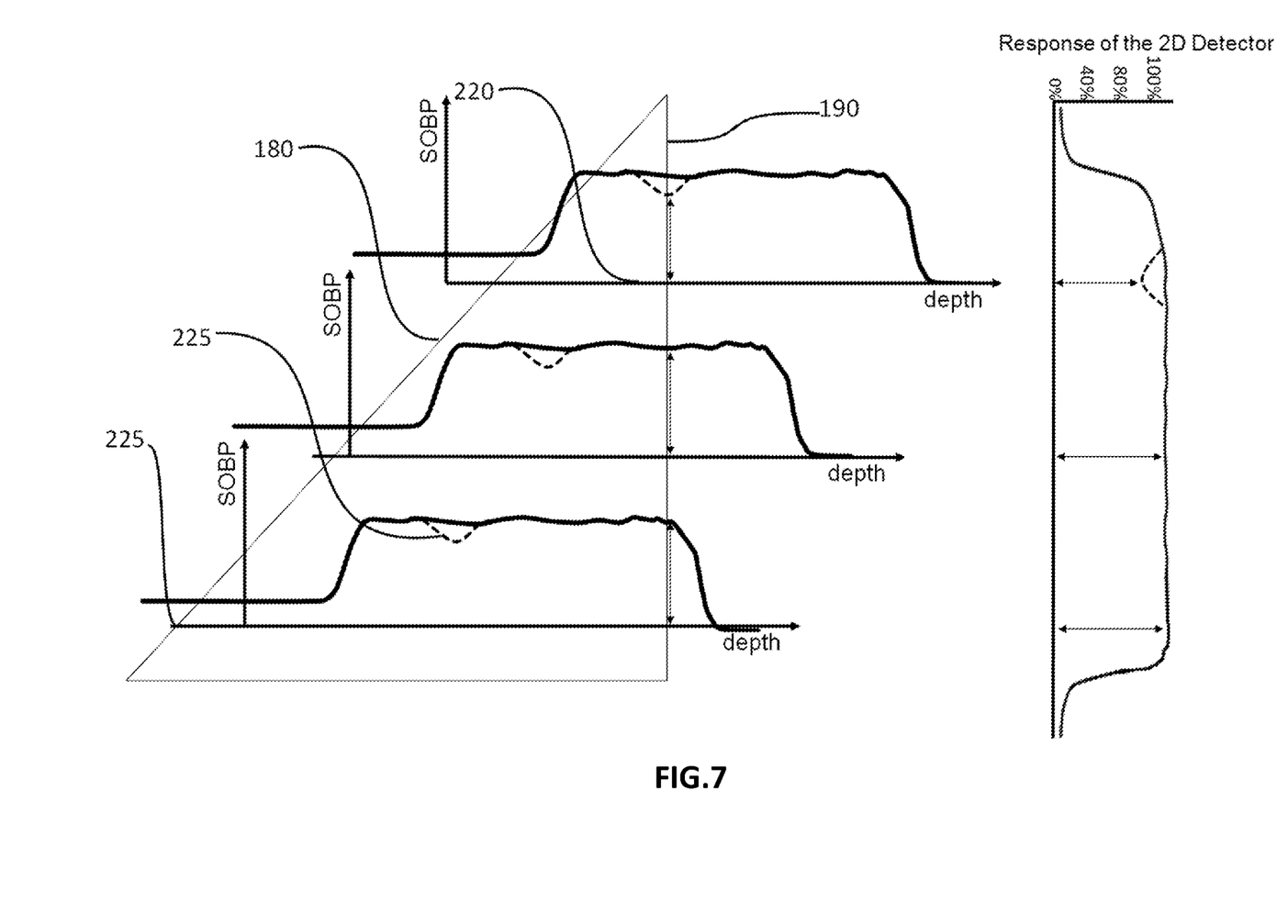
FIG. 7 is a schematic view of a modulated beam configured for producing an SOBP, traversing the SOBP wedge, at different heights, wherein a defect is present in the modulated beam.

FIG. 7 is similar to FIG. 6 with the difference that the SOBP has a defect 230, represented by a drop in the level of the SOBP at a certain depth, in dashed line. This might occur, e.g. if there was an error in the determination of the weight of one or more of the individual pencil beams used for making the modulated beam. This might occur also if there was a defect in the means used for modulating the energy such as a defect in the energy degrader. By using the device and method of the disclosure, such defects may be detected easily; as may be seen on the curve depicted at the right-hand side of FIG. 7, which shows a corresponding drop in the level of the response.

The phantom of the disclosure may be used as follows:
the phantom is positioned on the patient positioner. The phantom being light, and small this is an easy task. The phantom built according to the above description weights about 11 kg, including the 2D detector. The overall size of the phantom is 30×36×18 cm.
a modulated beam is directed at the SOBP wedges at a series of heights along the height of the SOBP wedged.
For each modulated beam, the response of the 2D detector is acquired, together with the corresponding heights.

From these acquired data, the actual SOBP is reproduced. The steps of directing a series of modulated beams, acquiring the data and displaying the resulting curve may be performed automatically under control of a controller.

Using the phantom of the disclosure, it is possible to efficiently and rapidly verify the functioning of components of the radiation therapy apparatus, including the means used for providing an SOBP. The acquired 2D doses may be processed by a program in order to compute a correction to be applied to the beams forming the SOBP.

The presence of a frame structure 30 in the phantom 10 of the disclosure has many advantages: the phantom may be manipulated easily, the frame is a reliable and precise reference for position of the various components of the phantom. Marks may be provided on the frame and used for aligning the phantom to laser beams or for visually aligning the phantom.

By using the phantom and method of the disclosure, it is possible to perform a daily verification of the functioning of a particle therapy apparatus, including components of said apparatus such as the positioning system, X-ray imaging system, beam directing system, dose, spot characteristics, uniformity in a reliable way. When performed under program control, the method is particularly efficient and fast, allowing to perform a full quality assurance in less than 10 minutes. With the method of the disclosure, the therapists save many time-consuming operations such as entering the treatment room for performing a change to a phantom and exiting the treatment room for performing the measurements.

The present disclosure has been described in terms of specific embodiments, which are illustrative of the disclosure and not to be construed as limiting. More generally, it will be appreciated by persons skilled in the art that the present disclosure is not limited by what has been particularly shown and/or described hereinabove. In the example embodiment discussed and shown on the figures, the inclined face of the wedges is oriented towards the beam source, while the perpendicular face of the wedges is oriented towards the 2D detector. However, it will be understood that positioning the wedges in the other orientation is equivalent. Also, the longest or the shortest side of the wedges may indifferently be positioned against the base plate.

Reference numerals in the claims do not limit their protective scope. Use of the verbs "to comprise", "to include", "to be composed of", or any other variant, as well as their respective conjugations, does not exclude the presence of elements other than those stated. Use of the article "a", "an" or "the" preceding an element does not exclude the presence of a plurality of such elements.

The invention claimed is:

1. A phantom for quality assurance of a hadron therapy apparatus usable in an intensity modulated particle therapy (IMPT) mode, said hadron therapy apparatus being configured for producing a hadron beam having an energy comprised between a low energy limit and a high energy limit, comprising:
   a frame structure comprising a base plate, the base plate having a first edge and a second edge parallel to said first edge;
   one or more energy wedges each having an energy wedge base face, an energy wedge first face inclined with respect to said energy wedge base face and an energy wedge second face perpendicular to said energy wedge base face,
   said one or more energy wedges being mounted on said base plate, said energy wedge second face being parallel to said second edge;
   a 2D detector arranged at said second edge, and being mounted perpendicular to said base plate;
   said one or more energy wedges, and said 2D detector being in known fixed positions in relation to said frame structure, wherein said phantom comprises a Spread-Out Bragg Peak (SOBP) wedge, said SOBP wedge having a SOBP wedge base face, an SOBP wedge first face inclined with respect to said SOBP wedge base face, and a SOBP wedge second face, perpendicular to said SOBP wedge base face, said SOBP wedge being mounted on said base plate, said SOBP wedge second face being parallel to said second edge,
   said SOBP wedge being made of a material having a density relative to water higher than 1.3,
   wherein a distance between said SOBP wedge first face and said SOBP wedge second face, measured along a line parallel to said SOBP wedge base face, varies between zero and a penetration depth in said material of a hadron beam having an energy equal to said high energy limit.

2. The phantom according to claim 1, wherein at least one of said one or more energy wedges is made of said material having a density relative to water higher than 1.3.

3. The phantom according to claim 1, wherein said material is selected from polyvinylidene fluoride, polyimides, polyetheretherketone polymers, and mixtures thereof.

4. The phantom according to claim 1, wherein said frame structure comprises one or two handles affixed to said base plate and to said 2D detector.

5. The phantom according to claim 1, wherein said 2D detector comprises an amorphous silicon active flat panel detector.

6. The phantom according to claim 1, wherein said base plate and one or more of said energy wedge base faces and/or said SOBP wedge base face comprise securing means for fixing said one or more energy wedges and/or said SOBP wedge to said base plate.

7. The phantom according to claim 1, wherein a distance between said first and said second energy wedge face of one of said one or more energy wedges, measured along a line parallel to said energy wedge base face is the penetration depth in said material of a hadron beam having a nominal energy between said high energy limit, and said low energy limit, at a middle of a height of said energy wedge, and is less than 15 mm lower at a bottom of said height of said energy wedge, and less than 15 mm higher at a top of said height of said energy wedge, wherein said height is a distance that is measured perpendicularly to said energy wedge base face.

8. A method for quality assurance of a hadron therapy apparatus usable in the intensity modulated particle therapy (IMPT) mode, said apparatus comprising a patient positioner having a reference position, using a phantom according to claim 1, the method comprising:
   a) positioning said phantom on said patient positioner;
   b) irradiating said phantom with a modulated beam, said modulated beam comprising a plurality of beams each having a different energy and having a dose selected in order to produce an SOBP in matter, said modulated beam being directed at said SOBP wedge first face, in a direction parallel to the SOBP wedge base face and at a height measured perpendicularly to said SOBP wedge base face
   c) acquiring a response of said modulated beam on said 2D detector;
   d) repeating b) and c) for a plurality of heights between the bottom height of said SOBP wedge, and the top height of said SOBP wedge;
   e) from said plurality of responses at each height, reconstructing the SOBP.

9. A non-transitory computer readable medium comprising code that, when executed, performs b) to e) of claim 8.

10. A system for the quality assurance of a hadron therapy apparatus comprising a phantom for quality assurance of a hadron therapy apparatus usable in the intensity modulated particle therapy (IMPT) mode, said hadron therapy apparatus being configured for producing a hadron beam having an energy comprised between a low energy limit and a high energy limit, comprising:
   a frame structure comprising a base plate, the base plate having a first edge and a second edge parallel to said first edge;
   one or more energy wedges each having an energy wedge base face, an energy wedge first face inclined with respect to said energy wedge base face and an energy wedge second face perpendicular to said energy wedge base face,
   said one or more energy wedges being mounted on said base plate, said energy wedge second face being parallel to said second edge;

a 2D detector arranged at said second edge, and being mounted perpendicular to said base plate;

said one or more energy wedges, and said 2D detector being in known fixed positions in relation to said frame structure, wherein said phantom comprises a Spread-Out Bragg Peak (SOBP) wedge, said SOBP wedge having a SOBP wedge base face, an SOBP wedge first face inclined with respect to said SOBP wedge base face, and a SOBP wedge second face, perpendicular to said SOBP wedge base face, said SOBP wedge being mounted on said base plate, said SOBP wedge second face being parallel to said second edge, said SOBP wedge being made of a material having a relative density higher than 1.3, a distance between said SOBP wedge first face and said SOBP wedge second face, measured along a line parallel to said SOBP wedge base face varying between zero and the penetration depth in said material of a hadron beam having an energy equal to said high energy limit, and a controller comprising a computer program according to claim 9.

11. The system according to claim 10, wherein said SOBP wedge of the phantom is made of a material having a density relative to water higher than 1.5.

12. The system according to claim 10, wherein said SOBP wedge of the phantom is made of a material having a density relative to water higher than 1.7.

13. The phantom according to claim 1, wherein said SOBP wedge is made of a material having a density relative to water higher than 1.5.

14. The phantom according to claim 1, wherein said SOBP wedge is made of a material having a density relative to water higher than 1.7.

15. The phantom according to claim 1, wherein at least one of said one or more energy wedges is made of said material having a density relative to water higher than 1.5.

16. The phantom according to claim 1, wherein at least one of said one or more energy wedges is made of said material having a density relative to water higher than 1.7.

* * * * *

UNITED STATES PATENT AND TRADEMARK OFFICE
CERTIFICATE OF CORRECTION

PATENT NO. : 11,554,273 B2  
APPLICATION NO. : 16/900133  
DATED : January 17, 2023  
INVENTOR(S) : Simon Marcelis et al.

Page 1 of 1

It is certified that error appears in the above-identified patent and that said Letters Patent is hereby corrected as shown below:

On the Title Page

Item (30), under "Foreign Application Priority Data," "19180094" should read --19180094.5--, and "19185261" should read --19185261.5--.

Item (57), Line 13 of ABSTRACT, "a SOBP" should read --an SOBP--.

In the Claims

Claim 1, Column 7, Line 51 and Line 53, "a SOBP" should read --an SOBP--.

Claim 10, Column 9, Line 7 and Lines 9-10, "a SOBP" should read --an SOBP--.

Signed and Sealed this  
Twenty-fifth Day of April, 2023

Katherine Kelly Vidal  
*Director of the United States Patent and Trademark Office*